United States Patent [19]
LeVeen et al.

[11] 4,201,209
[45] May 6, 1980

[54] MOLDED HYPODERMIC PLUNGER WITH INTEGRAL SHAFT AND ELASTOMERIC HEAD

[76] Inventors: Harry H. LeVeen, 800 Poly Pl., Brooklyn, N.Y. 11220; Robert F. LeVeen, 122 S. 51st St., Omaha, Nebr. 68132

[21] Appl. No.: 908,945

[22] Filed: May 24, 1978

[51] Int. Cl.² ............... B29D 9/00; B29F 1/00; A61F 5/315
[52] U.S. Cl. .............. 128/218 P; 222/386; 264/255; 264/259; 264/328
[58] Field of Search ........... 264/245, 250, 255, 328, 264/259, 171; 425/130; 128/218 P, 218 PA, 218 R, 220, 234, 237; 222/386, 391; 428/516, 518; 260/897 B

[56] References Cited
U.S. PATENT DOCUMENTS

| | | | |
|---|---|---|---|
| 3,051,994 | 9/1962 | Carozzo | 264/328 |
| 3,237,815 | 3/1966 | Ogle | 222/386 |
| 3,291,128 | 12/1966 | O'Neil | 222/386 |
| 3,348,546 | 10/1967 | Roberts et al. | 222/386 |
| 3,524,795 | 8/1970 | Petersen | 428/216 |
| 3,719,735 | 3/1973 | Valyi | 264/250 |
| 3,822,107 | 7/1974 | Wogerer | 264/245 |
| 3,966,866 | 6/1976 | Ballman et al. | 264/171 |
| 4,035,534 | 7/1977 | Nyberg | 428/516 |
| 4,082,877 | 4/1978 | Shadle | 428/518 |
| 4,116,914 | 9/1978 | Coran et al. | 260/897 B |

*Primary Examiner*—W. E. Hoag
*Attorney, Agent, or Firm*—Brooks, Haidt, Haffner, Delahunty

[57] ABSTRACT

Articles having portions of materials with different properties are integrally formed by injection of two different thermoplastic materials simultaneously through separate gates into the same mold wherein the materials fuse or bond together. A plunger for a syringe formed by the process has a rigid shaft and an elastomeric head.

1 Claim, 3 Drawing Figures

MOLDED HYPODERMIC PLUNGER WITH INTEGRAL SHAFT AND ELASTOMERIC HEAD

BACKGROUND OF THE INVENTION

1. Field of the Invention

The invention relates to injection molding, and more particularly to dual gate injection molding of articles having portions formed of different thermoplastic materials.

2. Description of the Prior Art

Methods are known for the extrusion or injection molding of laminated structures of mutually different thermoplastic materials, and for sequentially injecting or extruding different plastic materials into a mold or through a die to form products having parts with different characteristics.

Lefevre U.S. Pat. No. 3,528,310 relates to the coextrusion or simultaneous extrusion of a laminate of two or more parallel layers of different thermoplastic materials through concentrically related openings leading to a single extrusion orifice. Sawada et al U.S. Pat. No. 3,754,847 also relates to production of laminates by extrusion using separate passages for different materials leading to a common extrusion orifice.

The injection molding nozzle of Langecker U.S. Pat. No. 3,921,856 is described as simultaneously extruding a filling material and a cover material.

U.S. Pat. No. 3,809,519 to Garner relates to alternating sequential flow of materials through a single injection molding outlet by means of a valve.

Burlis et al U.S. Pat. No. 3,724,985 is concerned with the extrusion of tubing having portions of different materials along its axial length by sequential flow from two molten plastic producers through a single die.

Nye et al U.S. Pat. No. 3,776,674 relates to production of multi-colored articles by moving two separate discharge heads for the different colored materials over an open top mold cavity.

The references discussed all relate to forming articles from more than one material but none shows the use of two gates into a single mold for simultaneous injection of different thermoplastic materials to form a unitary article having portions with different characteristics.

It would be desirable to produce articles having portions with different properties in a single injection molding operation. One article which could be economically produced by such a technique is a unitary plunger for a syringe. Such plungers are usually produced by the mechanical assembly of two or more separately molded parts.

Disposable syringes have generally replaced the much more expensive ground glass syringes formerly used in medical practice, but the manufacture of such disposable syringes from plastic materials has involved certain difficulties.

The barrel of a syringe is of a length considerably greater than its radius, so in order to assure release of the barrel from an injection mold the barrel is formed with a slight taper from its open end to its closed end. A rigid cylindrical plunger sized to fit snugly within the open end of such a tapered barrel will become tightly wedged in place when advanced toward the closed end of the barrel and will lock in position before discharging the barrel contents through a cannula at the closed barrel end. Differential shrinkage of injection molded thermoplastic barrels results in inward bowing of the middle portion of the barrel between the barrel ends and thus further departure from uniform interior cross sectional area.

To overcome these irregularities of dimension, plungers for injection molded syringe barrels have been made with compressible gaskets or discs at their head ends to accommodate variations in barrel diameter and to avoid leakage around the plunger. Then discs or gaskets are typically made of rubber or other elastomeric material and then fitted on the barrel by stretching and snapping the elastomeric piece into place. The manufacture and assembly of two separately formed parts obviously tends to be less economical than would a technique of manufacture which required no assembly.

SUMMARY OF THE INVENTION

The process of the present invention produces unitary articles of two different thermoplastic materials by simultaneously injecting the molten materials into a mold through two separate, spaced gates. Within the mold the materials, if they are mutually compatible, fuse at a place of contact and the material that sets at each side of the contact zone has the characteristics of its constituent material. For example, in manufacturing the plunger of a syringe, the generally cylindrical barrel and outer end of the plunger can be formed of a substantially rigid non-toxic thermoplastic material such as high density polyethylene or polypropylene while the tip which seems to provide a seal can be formed of an elastomeric material such as vinyl acetate copolymer. These two materials are compatible in the sense that they fuse at a zone of contact within a mold into which they are simultaneously injected to produce an effectively unitary or integral article.

Even if thermoplastic materials which are not compatible in the sense described above are used for simultaneous injection into a single mold through spaced separated gates it is still possible to achieve a mechanical bond at the zone where the two different materials meet which is as satisfactory as that produced by separate formation and mechanical assembly of a rigid part and an elastomeric part.

It should be understood that various other kinds of articles may be advantageously produced by the process of the invention which is not limited to the manufacture of disposable syringe plungers, such plungers being an economically attractive example of one use of the process.

The mold employed according to the invention can be of any conventional type suited to the production of the intended product, except that there are two (or in some cases three or more) gates are provided to lead the thermoplastic material into different parts of the mold cavity. Conventional runner molds, or runnerless molds of various types with the usual clamp and ejection mechanisms can be employed.

Two separate injection molding machines, one for each of the different materials, are employed. More than two machines can be used if more than two materials are to be injected, or if more than two portions of different characteristics are to be provided in the molded article, for example in an article with a rigid middle portion and two elastomeric end portions.

For manufacturing the syringe plunger in accordance with the invention two injection molding machines are used. Each machine can be of known construction, for example of the inline reciprocating screw type. The nozzles of the two machines are arranged to inject the plastic material in metered amounts into the separated gates of the mold, so that at one end portion the mold cavity is filled with elastomeric material, and the rest of the cavity being filled with material that becomes rigid upon setting, the space where the different materials meet within the cavity being a zone of fusion of the two materials upon setting. The resulting unitary article is ejected and the apparatus is ready for another cycle.

These and other features, adaptations and advantages of the present invention will be more fully understood from the following detailed description of preferred embodiments especially when the description is read in conjunction with the accompanying drawing figures.

BRIEF DESCRIPTION OF THE DRAWINGS

In the drawings, wherein like reference characters designate like parts throughout.

DETAILED DESCRIPTION OF PREFERRED EMBODIMENTS

Figure 1:
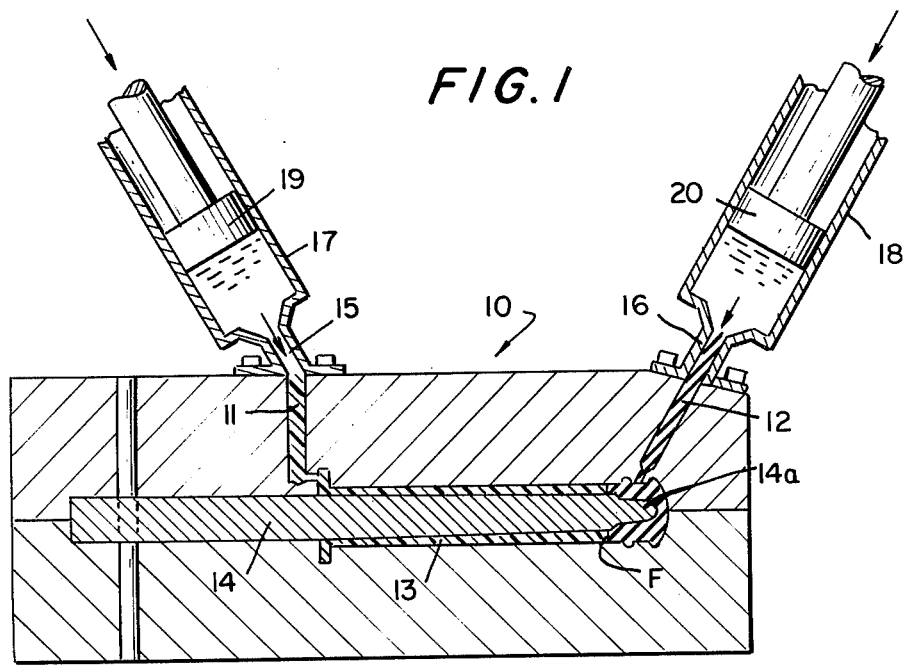
FIG. 1 is a somewhat schematic illustration of a mold as used in the process of the invention.

FIG. 1 schematically illustrates the filling of a mold generally designated by reference numeral 10 through two gates 11 and 12 with two different thermoplastic materials. The mold cavity 13 is shown as generally cylindrical with an axially extending core pin 14 to shape a plunger as shown in FIG. 2 for a syringe of the kind shown in FIG. 3.

In the simplified illustration of FIG. 1 thermoplastic material is shown being injected through nozzles 15 and 16 of two injection molding machine cylinders having reciprocally movable rams 19 and 20 respectively for forcing plasticated material through the gates 11 and 12. Heating and plasticating means are not illustrated, since conventional equipment can be employed for the purpose. For example, reciprocating screw type injection molding machines can be used. For simplicity of illustration machine details are omitted, but it should be understood that machines operative to heat and deliver selected thermoplastic materials are available and the choice of such equipment is well within the skill of those familiar with injection molding techniques.

Figure 2:
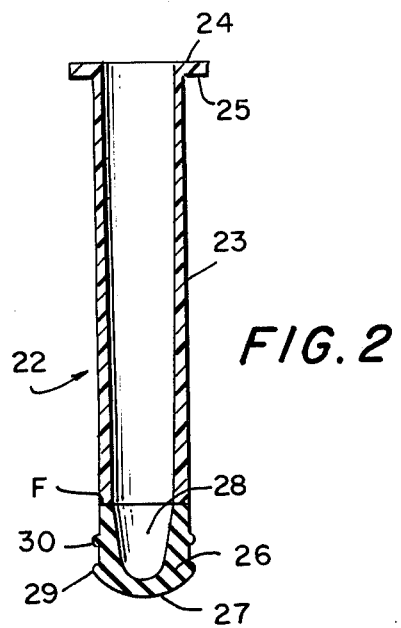
FIG. 2 is a view in section of a product produced by the process of the invention, a plunger for a syringe.

FIG. 2 is a view in section of a plunger for a disposable syringe, generally designated by reference numeral 22. The plunger 22 has a hollow substantially cylindrical body 23 terminating at an open end 24 in an annular lip or flange 25. A head portion 26 of the plunger 22 closes the cylindrical body 23 at the end opposite from the open end 24.

The plunger head portion 26 is generally cylindrical with a convex outer face 27 closing a central cavity 28 formed by the end 14a of the core pin 14 as an extension of the interior opening of the plunger body 23. Throughout most of its length the plunger head portion 26 has the same cross sectional area as the plunger body 23 but at the periphery of the convex outer face 27 the head portion 26 has an integral circumferentially extending lip 29 of larger diameter than the plunger body 23. Another similar circumferential lip 30 is provided on the head portion 26 near the location of the generally flat inner face 28 and close to the zone where the head portion 26 joins the plunger body 23.

For strength and regidity the plunger body 23 and flange 25 are formed of a relatively hard thermoplastic material such as high density polypropylene or polyethylene, whereas the plunger head portion 26 is formed of an elastomeric material, for example ethylene vinyl acetate copolymer.

The plastic materials forming the plunger body portion 23 and head portion 26 can be considered compatible if both materials are non-polar or if both are polar, but generally speaking polar plastics will not fuse satisfactorily with non-polar plastics. As one example of two plastics which can be used are polypropylene CD-460 produced by E. I. DuPont de Nemours & Co. and ethylene vinyl acetate EVA 3185 produced by Exxon Chemical Co. Nylon and thermoplastic urethanes such as Celanese 1300 Nylon 6/6 and polyurethane Estane 58121 manufactured by B. F. Goodrich Chemical Co. are also compatible.

Figure 3:
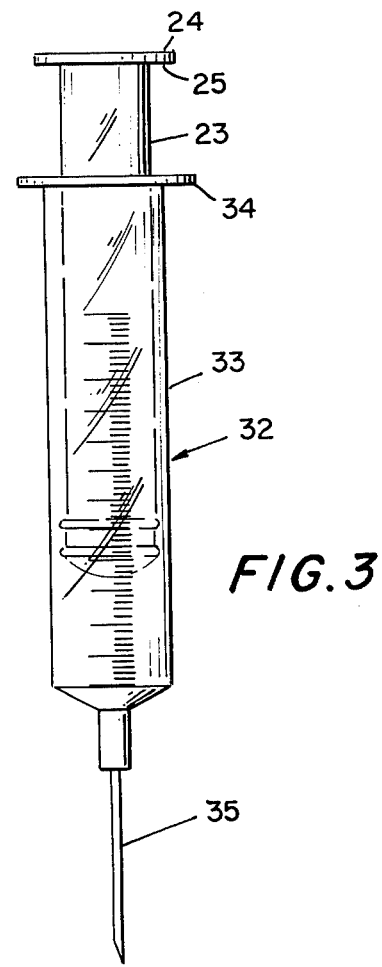
FIG. 3 is an overall view of a syringe employing the plunger of FIG. 2.

The elastic properties of the head portion 26 cause the outwardly projecting lips 29 and 30 to function effectively as seals against fluid leakage when the plunger 22 is fitted slidably in a syringe body of the type shown in FIG. 3 and generally designated 32.

It will be seen that the barrel portion 33 of the syringe body 32 has an open cylindrical space sized to closely yet slidably receive the plunger 22 with the circumferential lips 29 and 30 slightly compressed to provide a fluid tight seal. The syringe barrel portion 33 and a flange 34 at the open end of the syringe 32 are preferably formed of clear rigid plastic material, which can desirably be the same material as that which constitutes the body 23 of the plunger 22. The syringe 32 is shown equipped with a cannula 35 of the usual kind, and can be so economically made as to be disposable after a single use. Indicia of displaced volume can be provided as shown on the syringe barrel 33, and the plunger is preferably of such length that the syringe contents are fully discharged when the flange 25 of the plunger is still some distance away from the flange 34 of the syringe body 32.

To facilitate manufacture, and in particular to aid in ejecting the plunger 22 from a mold 10, the plunger body 23 can be slightly tapered rather than perfectly cylindrical, narrowing slightly toward the head portion 26. The sealing lips 29 and 30 will prevent leakage of fluid even though the plunger is not in close contact with the inner wall of the syringe body 33 throughout its length.

Reverting to FIG. 1 showing the manner of manufacturing articles such as the plunger 22, it will be seen that thermoplastic material injected through the gate 11 moves through the mold cavity 13 to fill the volume around the core pin 14, while other thermoplastic material simultaneously forced into the mold cavity 13 through the gate 12 moves to fill the other end of the mold cavity 13. At the zone indicated at F in FIG. 1 the two masses of plastic material meet, mingle and fuse during cooling to form a unitary article. By controlling the rates of injection of the two materials into the mold cavity 13, the zone of fusion F can be produced at the desired location. In the case of the plunger shown in FIG. 2, this zone of fusion is located to the rear of the circumferential lip 30 of the head portion 26.

Because all plastics do not have the same melt index, and because the volumes of the mold cavity to be filled by the different materials may be different, the timing of injection may not be exactly synchronous. That is, the injection of one of the plastic materials may begin before the other, where the first material is to fill a larger volume or does not flow as readily as the second. However injection of both plastic materials is simultaneous in the sense that the two materials meet at the fusion zone F. Another procedure for controlling the location of the fusion zone F is to employ different injection pressures for the different materials. Timing and pressure can both be varied to accomplish good fusion at the desired location in a single cycle.

The molding temperatures of different materials also differ, but since separate molding machines are used for the different materials, individual temperature control for each material is readily accomplished.

Various modifications of the apparatus and method shown and described will suggest themselves to those acquainted with injection molding. For example, more than two gates could be provided to produce an article having more than two portions of different characteristics from the adjacent portions, such as an article with a rigid center portion and two ends of elastomeric material, or an article with a flexible middle portion and rigid ends. These and other modifications and adaptations of the invention are considered to be within the spirit and scope of the invention.

What is claimed is:

1. A molded plunger for a hypodermic syringe having a rigid thermoplastic shaft and a head portion made of a thermoplastic polymer having elastomeric properties compatible with the material of said shaft and integrally united therewith by co-injection molding the materials of said shaft and said head.

* * * * *